(12) United States Patent
Fumiyoshi et al.

(10) Patent No.: US 6,358,700 B2
(45) Date of Patent: *Mar. 19, 2002

(54) METHOD FOR DETECTING MICROORGANISMS BY FLUORESCENT STAINING USING HYDROSTATIC PRESSURE

(75) Inventors: Abe Fumiyoshi; Koki Horikoshi, both of Yokosuka (JP)

(73) Assignee: Japan Marine Science and Technology Center, Yokosuka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/190,168

(22) Filed: Nov. 12, 1998

(51) Int. Cl.$^7$ .............................. C12Q 1/04; C12Q 1/02; C12N 1/16

(52) U.S. Cl. ..................... 435/34; 435/29; 435/255.21

(58) Field of Search ..................... 435/34, 29, 173.8, 435/255.21; 436/172

(56) References Cited

U.S. PATENT DOCUMENTS 5,545,535 A  *  8/1996  Roth et al. ..................... 435/34

OTHER PUBLICATIONS

Abe et al., Vacuolar acidification under high hydrostatic pressure in *Saccharomyces cerevisiae*. Prog. Biotechnol. 13 (High Pressure Bioscience and Biotechnology), pp. 53–58. (1996). No month found.*

Breeuwer et al., Characterization of uptake and hydrolysis of fluorescein diacetate and carboxyfluorescein diacetate by intracellular esterases in *Saccharomyces cerevisiae*, which result in accumulation of fluorescent product. Applied and Environ. Microbiol. 61 (4), pp. 1614–1619. (Apr. 1995).*

Crenshaw et al., Hydrostatic pressure has different effects on the assembly of tubulin, actin, myosin II, vinculin, talin, vimentin, and cytokeratin in mammalian tissue cells. Experimental Cell Research 227, pp. 285–297. (1996). No month given.*

Abe et al., Hydrostatic pressure promotes the acidification of vacuoles on *Saccharomyces cerevisiae*. FEMS Microbiol. Letters 130 (2–3), pp. 307–312. (Aug. 1995).*

Abe, F., *Applied & Environmental Microbiology*, 64(3):1139–42 (Mar. 1998).

* cited by examiner

*Primary Examiner*—Michael P. Woodward
*Assistant Examiner*—Marjorie A. Moran
(74) *Attorney, Agent, or Firm*—Burns, Doane, Swecker & Mathis, LLP

(57) ABSTRACT

A method for detecting microorganisms present in a sample comprises the steps of: applying a non-lethal hydrostatic pressure to a sample containing microorganisms; and staining the microorganisms with a fluorescent dye. The method permits a significant increase in the uptake of a fluorescent substance by applying, to a sample, a desired non-lethal hydrostatic pressure, without causing any reduction of the survival rate of microorganisms. The method also permits the elimination of such a secondary effect that the subject microorganism undergoes proliferation during staining the same with a fluorescent dye. Thus, the present invention would contribute to the determination of the correct viable count in a wide variety of technical fields.

5 Claims, 4 Drawing Sheets

US 6,358,700 B2

METHOD FOR DETECTING MICROORGANISMS BY FLUORESCENT STAINING USING HYDROSTATIC PRESSURE

FIELD OF INVENTION

The present invention relates to a method for detecting microorganisms and, in particular, to a high sensitive method for detecting microorganisms by the flow cytometry.

BACKGROUND OF INVENTION

To determine total viable cell number present in an interested sample is a very important subject in a wide variety of technical fields such as various examinations of food materials possibly contaminated with pathogenic microorganisms and infectious cases or inspection of harmful planktons causing the red tide. On the other hand, when understanding the circulation of substances and energy, it would be very important to recognize the biomass of microorganisms having an important function as decomposers in the ecosystem from the viewpoint of the basic research.

The flow cytometry is a method in which isolated cells are suspended in a medium, then passed through a flow cell at a high speed and subjected to a variety of measurements using optical means. The flow cytometry has become of major interest recently as a quite powerful tool for quickly and correctly counting the number of microorganisms present in a sample, in cooperation with the development of novel fluorescent dyes for staining biological cells. Thus, the flow cytometry has widely and rapidly been used in both the inside and outside of the country for some years ahead as an epoch-making technique that may supersede the colony-counting method and the quantitative ATP-analysis. In this method, it is an absolutely necessary condition that the microorganisms present in the sample are surely stained by the fluorescent dye and the intensity of the fluorescent light rays emitted when the sample passes through a superfine tube is determined by a highly sensitive detector. However, the amount of the fluorescent dye taken by the microorganism widely varies depending on the kind thereof and, in particular, when the amount is considerably lower than the detection limit of the flow cytometry, it has been indicated that it is difficult to correctly determine the viable cell count.

More specifically, it is widely recognized that fluorescence labeling of microorganisms is an effective means to determine the total cell number or how many viable cells exist in a sample. The flow cytometry combined with the fluorescence staining technique has been known as a powerful means to analyze heterogeneous microbial populations (see, for instance, Reference Nos. 7 and 11). Fluorescein diacetate (FDA) and the derivatives thereof are non-fluorescent molecules that defuse into cells and are hydrolyzed by intracellular non-specific esterases to give fluorescent products. The fluorescent products can be accumulated only in those cells that have intact cell membranes, therefore, dead cells with leaky membranes are not stained. Breeuwer et al. (see, for instance, Reference Nos. 5 and 6) reported the precise kinetics of membrane transport and intracellular hydrolysis of FDA and carboxyfluorescein diacetate (CFDA) as determined in studies aimed to optimize fluorescence staining for the detection of yeast cells in food materials by the flow cytometry. However, the fluorescent intensity of labeled cells varies considerably depending on the kinds of strains, probably because of differences in intracellular esterase activities. This may cause inaccuracy in detection of yeast cells in heterogeneous populations by the flow cytometry. Recently, the inventor has found by chance that the accumulation of carboxyfluorescein (CF) or carboxydichlorofluorescein (CDCF) in the cells was facilitated by the application of a hydrostatic pressure of the non-lethal level. Hydrostatic pressure is a thermodynamic variable that acts to decrease the total volume of a system at equilibrium in the case of liquids and solutions. Although the physicochemical basis of the effect of the hydrostatic pressure is well-established (see, for instance, Reference Nos. 2 and 8), the pressure-induced phenomena that occur in living microorganisms have not yet been fully defined.

SUMMARY OF THE INVENTION

Accordingly, it is an object of the present invention to provide a highly sensitive method for detecting the number of microorganisms present in a sample, by the flow cytometry.

It is another object of the present invention to provide a method for increasing the amount of fluorescent dye taken into microorganisms.

According to the present invention, there is thus provided a method for detecting microorganisms present in a sample which comprises the steps of (a) applying a non-lethal hydrostatic pressure to a sample containing microorganisms; and (b) staining the microorganisms with a fluorescent dye.

According to another aspect of the present invention, there is also provided a method for increasing the uptake of fluorescent dye molecules by microorganisms present in a sample, which comprises the step of applying a non-lethal hydrostatic pressure to the sample containing the microorganism.

DESCRIPTION OF PREFERRED EMBODIMENTS

Figure 1:
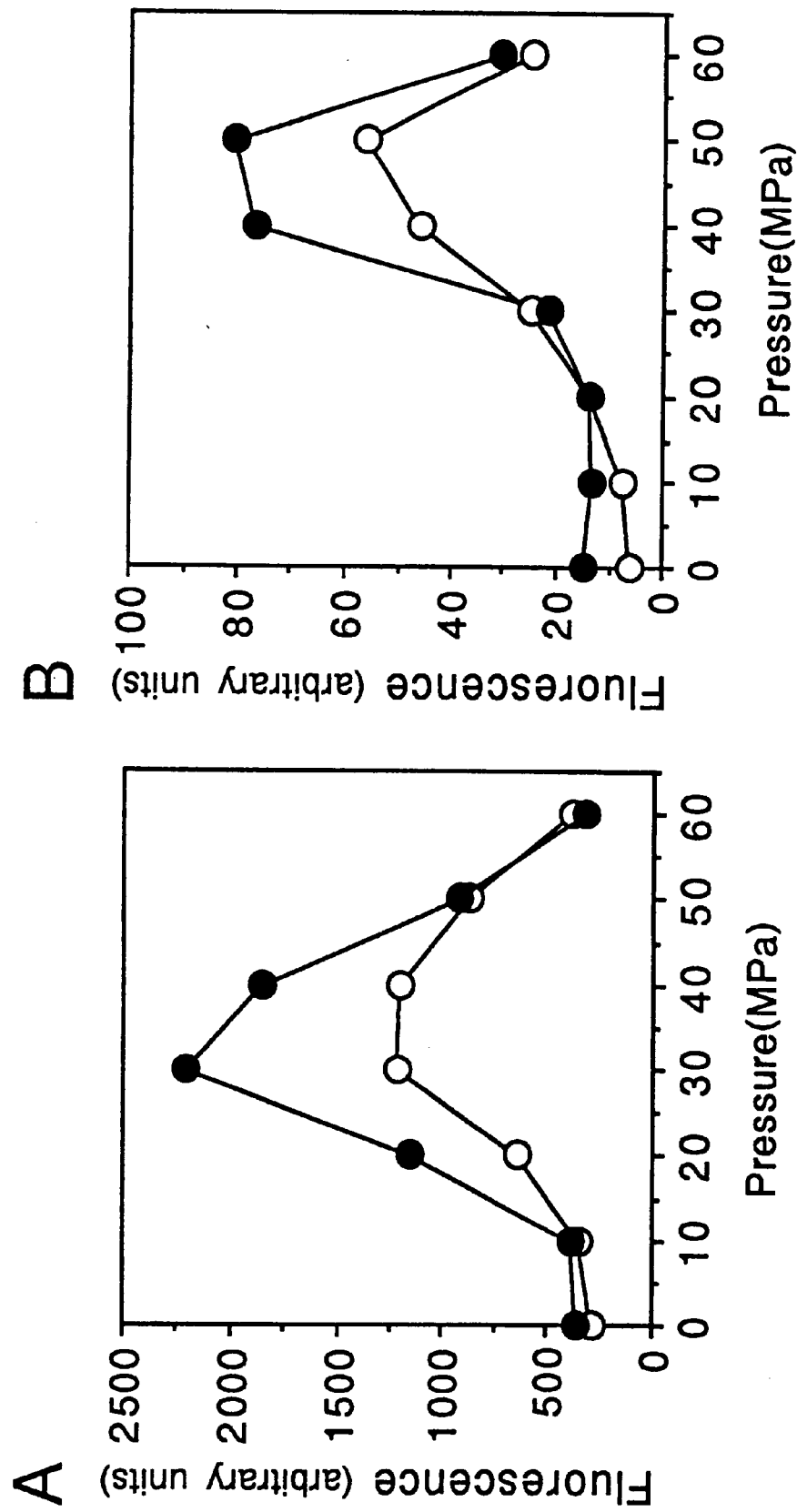
FIG. 1 is a diagram showing the hydrostatic pressure-induced CF and CDCF accumulation i the strains IFO2347 (A) and IFO10159 (B). ○: Cells stained with CF; ●: Cells stained with CDCF.

In the present invention, the hydrostatic pressure to be applied is not limited to any specific range so far as it is non-lethal to microorganisms to be examined and preferably ranges from 10 to 100 MPa (about 100 to 1000 atm), more preferably 10 to 60 MPa (about 100 to 600 atm) and most preferably 30 to 50 MPa (about 300 to 500 atm).

The rate of reduction and increase of the hydrostatic pressure each is not restricted to any specific range inasmuch as it does not adversely affect the survival rate of microorganisms and the uptake of a fluorescent dye by the same. The rate of increase in the hydrostatic pressure desirably ranges from about 0.1 to 1.0 MPa/sec, while the rate of reduction in the hydrostatic pressure desirably ranges from about 0.1 to 1.0 MPa/sec.

When the hydrostatic pressure reaches a desired level, the culture is allowed to stand for 0.1 to 5 hours, preferably 0.5 to 3 hours and then the pressure is reduced to ordinary pressure.

The present invention can be applied to all sorts of microorganisms and cells capable of being stained with fluorescent dyes- One of the typical examples of microorganisms to which the present invention can be applied is yeast. However, the present invention can likewise be applied to microorganisms other than yeast, for instance, bacteria such as E. coli and Vibrios, molds such as Penicilliums and Aspergilluses, planktons such as Gymnodiniums and cultivated cells derived from animals and plants.

The fluorescent dyes usable in the present invention are not restricted to specific ones and examples thereof are as follows: ethidium bromide, propidium iodide, Hoechst 33258/33342, DAPI, Acridine orange, Chromomycin, Mithramycin, Olivomycin, Pyronin Y, Thiazole orange, FITC, Rhodamine 101 isothiocyanate, BCECF, BCECF-AM, C.SNARF-1, C-SNARF-1-AMA, Aequorin, Indo-1, Indo-1-AM, Fluo-3, Fluo-3-AM, Fura-2, Fura-2-AM, Oxonol, Rhodamine 123, 10-N-nonyl-acridine orange, Florescein, Fluorescein diacetate, Carboxyfluorescein (CF), Carboxyfluorescein diacetate (CFDA), Carboxydichlorofluorescein (CDCF), and Carboxydichlorofluorescein diacetate (CDCFDA).

The amount of these fluorescent dyes to be used in the sample liquid is desirably about 1 to 100 $\mu$M.

In the present invention, the steps of (a) applying a non-lethal hydrostatic pressure to a microorganism-containing sample and (b) staining the microorganism with a fluorescent dye may be carried out in any order. Alternatively, these steps (a) and (b) may be simultaneously be carried out or these steps may be alternately be repeated over several times.

In addition, when a hydrostatic pressure is applied to a sample in the co-existence of glucose, the staining of the microorganism with the dye can be accelerated. In this case, the amount of glucose desirably ranges from about 10 to 100 mM based on the sample liquid.

Moreover, the step for staining microorganisms with a fluorescent dye should be carried out under the conditions which result in the inhibition of the proliferation thereof and do not result in the reduction of the survival rate of the microorganisms. In case of yeast, it is sufficient to incubate the microorganism-containing sample at a temperature ranging from 15 to 37° C. for 0.1 to 5 hours with or without applying a desired hydrostatic pressure thereto.

The present invention will further be described in more detail with reference to the following non-limitative working Examples, but the present invention is not limited to these specific Examples at all.

<Cell Culture and Application of Hydrostatic Pressure>

Cells of Saccharomyces cerevisiae were grown in YPD (1% yeast extract, 2% bactopeptone, 2% D-glucose) broth at 24° C. Cells from a log-phase culture ($2 \times 10^7$ to $4 \times 10^7$ cells/ml) were collected by centiifugation and re-suspended in fresh YPD containing 50 mM citric acid (pH 3.0 or pH 5.0), then placed in plastic tubes (Cryotubes, available from Nunc) at $2 \times 10^7$ to $3 \times 10^7$ cells/ml. After sealing with Parafilm, the tubes were put into titanium pressure vessels, followed by application of a desired hydrostatic pressure. The each required hydrostatic pressure was established within 2 min using a hand pump (available from Rigo-sha, Japan). To remove samples, the pressure was released in approximately 15 sec.

In a preliminary experiment, the adiabatic decompression from 60 MPa to 0.1 MPa reduced the temperature of the MB buffer (100 mM MES (moipholinoethanesulfonic acid)—Bis-Tris (bis(2-hydihoxyethyl)iminotris-(hydroxymethyl) methane), pH 5.0) by approximately 0.5° C. Such a small change in temperature is negligible. In fact, no significant difference was observed in both cell viability and accumulation of fluorescent dyes, even when compression and decompression operations were rapidly carried out (data not shown).

<Labeling (or Staining) of Cells with Fluorescent Dyes>

Cells originated fiom a log-phase culture ($2 \times 10^7$ to $4 \times 10^7$ cells/ml) were incubated with 10 $\mu$M CFDA (Sigma, Cat. No. C-5041) in YPD containing 50 mM citric acid (pH 3.0), or 10 $\mu$M CDCFDA Molecular Probe, Cat. No. C-369) in YPD containing 50 mM citric acid (pH 5.0), respectively, under varying hydrostatic pressures ranging from ordinary pressure to 60 MPa. To analyze the dependence, on glucose, of pressure-induced dye-accumulation, vegetative cells were collected, washed twice in distilled water and starved for 30 min on ice. Then cells were suspended in MBA buffer (100 mM MES-Bis-Tris, 100 mM ammonium sulfate, pH 5.0), followed by addition of CDCFDA and application of a desired hydrostatic pressure of up to 6OMPa for one hour in the presence of D-glucose in various concentrations.

To analyze the effect of 2-deoxyglucose, cells were incubated with CDCFDA in MBA buffer containing 100 mM D-glucose. Unless otherwise specified, the final concentration of the fluorescent dye was 10 $\mu$M. After applying a desired hydrostatic pressure for one hour, the cells were washed twice with 10 mM MES-Bis-Tris (pH 5.0) and suspended in MB buffer. Fluorescence of the labeled cells emitted at 535 nm with excitation at 485 nm was detected using CytoFluor 2350 Plate Reader (available from Mlipore), or an RF5300PC spectrofluorometer (available from Shimazu, Japan). Fluorescence intensity (a. u.; arbitrary units) was recorded as the fluorescence of labeled cells minus the fluorescence of non-labeled cells for $10^7$ cells.

<Fluorescence Analysis under Hydrostatic Pressure>

Fluorescence emission was examined under several hydrostatic pressures in a hydrostatic chamber provided with transparent windows which were made by sapphire (size: 10×8 mm). Each sample in a transparent cuvette was placed in the chamber which was set up in an RF5300PC spectrofluorometer. Fluorescence was emitted at 535 nm with excitation at 485 nm. The fluorescence intensity of the labeled cells was strong enough to be detected through the sapphire windows, even though the emission was reduced compared to the analysis without such a hydrostatic chamber equipped with a sapphire window. Each hydrostatic pressure was applied using a hand pump (available from Teramecs, Co. Ltd., Japan).

<Flow cytometry>

Cells were incubated with 10 $\mu$M CFDA or 10 $\mu$M CDCFDA and cultivated under several hydrostatic pressures for one hour. After decompression, the labeled (or stained) cells were washed twice with distilled water and re-suspended in MB buffer. The cells were analyzed using the Bryte-HS Flow Cytometry System (available from Bio-Rad) under ordinary pressure.

EXAMPLE 1

Accumulation of CF and CDCF Under Elevated Hydrostatic pressure

CFDA and CDCFDA are known to be hydrolyzed by intracellular non-specific esterases, and the resulting fluorescent products, i.e., CF (pH-sensitive) and CDCF (pH-insensitive) are accumulated in intracellular acidic compartments such as vacuoles (see Reference Nos. 9 and 10). CDCFDA is rather useful for labeling of viable cells because it is more stable than CFDA in a less acidic medium (pH~5.0), and the molar fluorescence intensity of the hydrolysis product CDCF observed at 530–540 nm is greater than that of CF.

Since the degree of the fluorescent staining may vary depending on the kinds of strains, two kinds of strains, i.e., the sake yeast IFO2347 (a strongly labeled strain) and IFO10159 (a weakly labeled strain, which is less readily detectable by the flow cytometry), were used in this study.

Cells of the IFO2347 strain were incubated with 10 $\mu$M of CFDA or CDCFDA and cultured for one hour under each hydrostatic pressure condition. The stained cells were analyzed using Cytofluor 2350. The results thus obtained are plotted on FIG. 1A Similarly, cells of IFO10159 strain were inoculated with 10 $\mu$M of CFDA or CDCFDA and cultured for one hour under each hydrostatic pressure condition. The stained cells were analyzed using Cytofluor 2350. The results thus obtained are plotted on FIG. 1B. In FIGS. 1A and 1B, ○ and ● represent cells stained with CF and those stained with CDCF, respectively.

It was found that the application of hydrostatic pressure markedly promoted the accumulation of CF and CDCF in the IFO 2347 strain and peaks were observed at 40 MPa and 30 MPa, respectively (FIG. 1A). It was also observed that the degree of pressure-induced accumulation of CDCF was greater than that observed for CF in the cells. Thus, CDCFDA was mainly used for labeling in the following experiments.

The total fluorescence intensity, observed for the cells of the IFO10159 strain which were labeled with CF at ordinary pressure (15.5 a. u. per $10^7$ cells), was only 1.6-fold greater than that observed for non-labeled cells (9.6 a. u. per $10^7$ cells), i.e., the self-fluorescent intensity of the background, and CDCF-labeled cells (24.8 a. u. per $10^7$ cells) was about 2.5-fold greater than that observed for non-labeled cells (9.9 a. u. per $10^7$ cells). It was found that a pressure of 50 MPa enhanced the accumulation of dyes five to ten folds (FIG. 1B). No considerable change was observed in the self-fluorescence of non-labeled cells at 50 MPa. Although there are no data to explain that the five to ten fold-enhancement would have a significant impact on detection limits in natural samples, application of moderate hydrostatic pressure could be potentially a new procedure for detection of living yeast cells.

A hydrostatic pressure above 40 MPa markedly inhibited cell growth. However, the survival rate determined in terms of the relative CFU (colony forming units) was not considerably affected by application of a hydrostatic pressure for only one hour (see Reference No. 1). Therefore, it is evident that the application of a hydrostatic pressure during staining can increase the degree of staining with CF or CDCF while preventing cell proliferation or significant loss of viability during the treatment. This is quite advantageous for precise determination of viable cell number present in a sample.

EXAMPLE 2

Analysis According to Flow Cytometry

Figure 2:
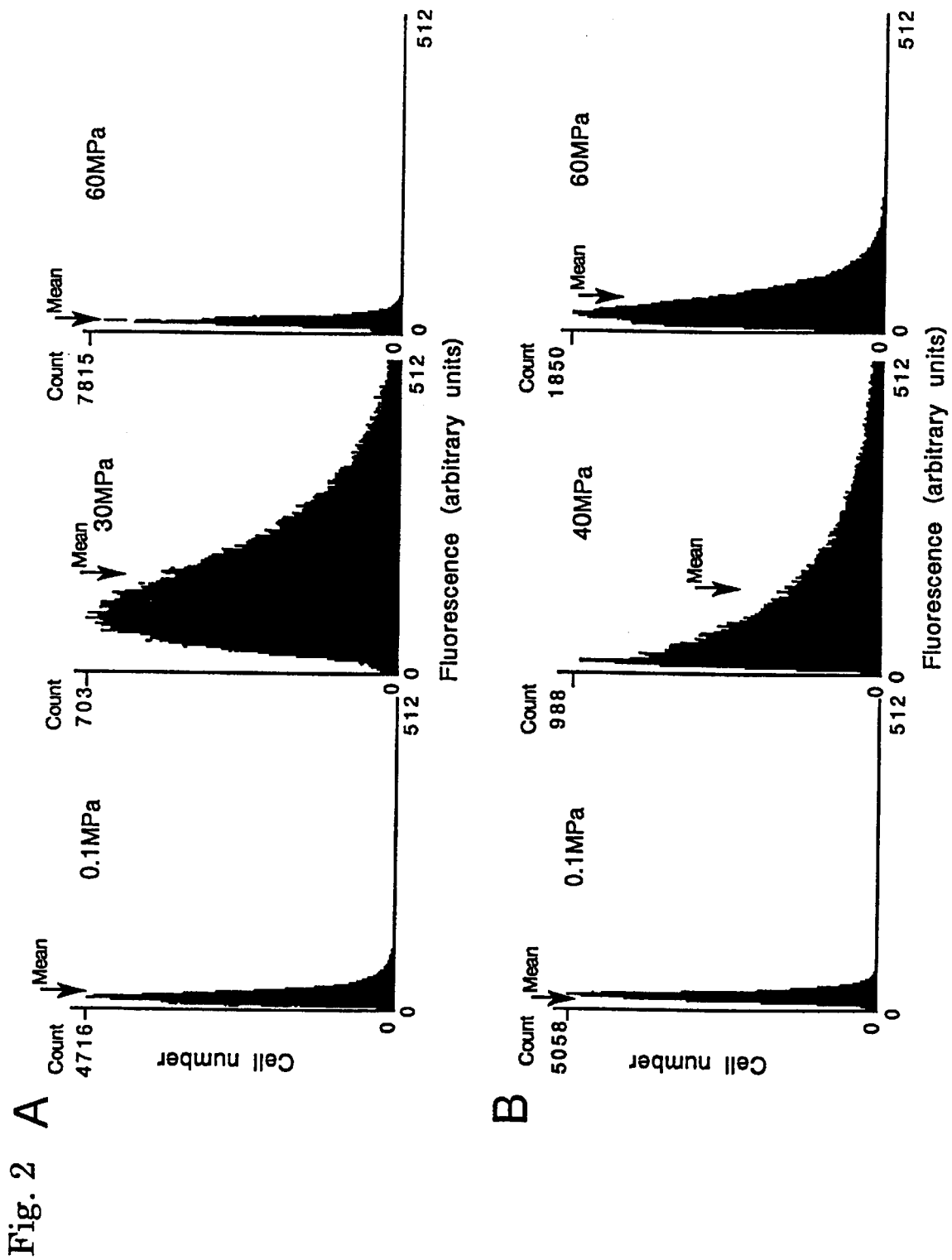
FIG. 2 is a diagram showing the histograms of populations of IFO2347 (A) and IFO10159 (B) cells stained with CDCFDA under various hydrostatic pressures.

The IFO2347 strain was cultured at 24° C. for one hour in the presence of 10 $\mu$M CDCFDA, under a hydrostatic pressure of 0.1, 30 or 60 MPa. The CDCFDA-labeled cells (about 100,000) were analyzed using the Bryte-HS Flow Cytometry System. FIG.2A depicts the histograms showing the intensity distribution of populations of IFO2347 cells labeled with CDCFDA observed after the cultivation.

In addition, the IFO10159 strain was cultured at 24° C. for one hour in the presence of 10 $\mu$M CDCFDA, under a hydrostatic pressure of 0.1, 40 or 60 MPa. The CDCFDA-labeled cells (about 100,000) were analyzed using the Bryte-HS Flow Cytometry System. FIG.2B depicts the histograms showing the intensity distribution of populations of IFO2347 cells labeled with CDCFDA observed after the cultivation.

When the IFO2347 cells were labeled at ordinary pressure, the peak (the number of labeled cells is largest at this fluorescent intensity) and mean (the average upon integration) fluorescence of labeled cells were 23 a.u. and 26 a.u., respectively (FIG. 2A, 0.1 MPa). It was found that when applying, to the cells, a hydrostatic pressure of 30 MPa for one hour, the accumulation of CDCF increased four to six folds. In this case, the peak and mean fluorescence were found to be 92 and 162 a.u., respectively (FIG. 2A, 30 MPa). However, staining was not enhanced at a hydrostatic pressure of 60 MPa (FIG. 2A, 60 MPa).

Similar results were also obtained for the IFO10159 strain (FIG. 2B). Almost the same results were obtained when the cells were incubated with CFDA (data not shown).

These results of the flow cytometric analysis are mostly consistent with the results obtained by the ordinary fluorescence analysis shown in FIG. 1.

EXAMPLE 3

Effects of Hydrostatic Pressure on Hydrolysis of CDCFDA

Figure 3:
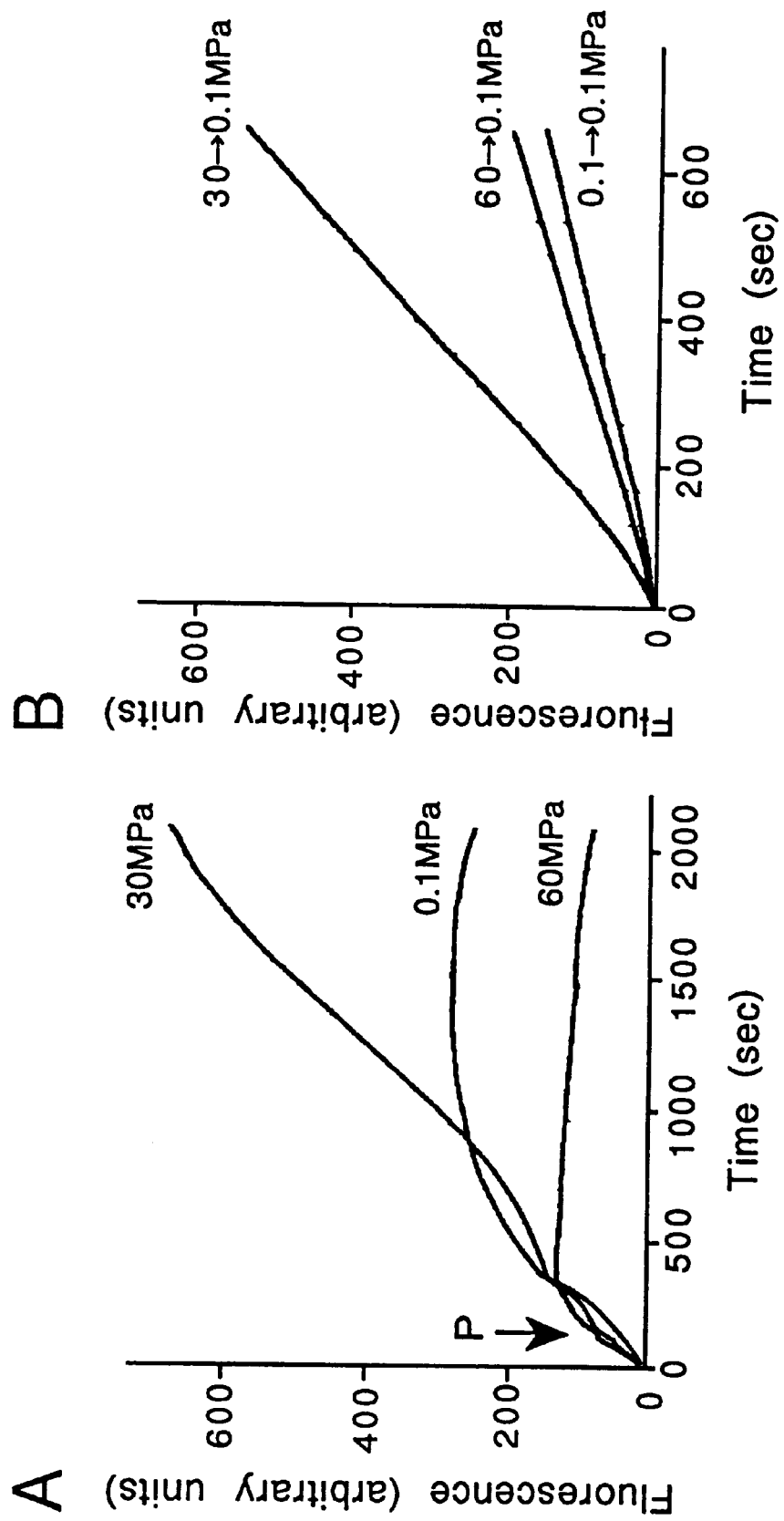
FIG. 3 is a diagram showing the effects of the hydrostatic pressure on the hydrolysis of CDCFDA observed for the stain IFO2347. (A): The hydrolysis of CDCFDA under the influence of a pressure; (B): The hydrolysis of CDCFDA under the usual pressure observed for cells which are pre-treated at each pressure condition.

A cuvette containing the IFO2347 strain was fitted to a container, followed by addition of 50 $\mu$M CDCFDA, application of a hydrostatic pressure at a point P (see FIG. 3A), and examination of the fluorescence intensity change with time in a hydrostatic chamber equipped with RF5300 Fluorescent Spectrometer. The results obtained are plotted on FIG. 3A The fluorescence intensity increased to 300 a.u. and 130 a.u. when hydrostatic pressures of 0.1 MPa (ordinary pressure) and 60 MPa were applied, respectively (FIG. 3A). On the other hand, the fluorescence intensity increased to 770 a.u. when a pressure of 30 MPa was applied.

Cells of the IFD2347 strain were pre-incubated at several hydrostatic pressures for one hour in YPD culture medium (pH 5.0), and subsequently the pre-incubated cells were placed into a cuvette, followed by addition of 50 $\mu$M of CDCFDA to the pressure-adapted cells at ordinary pressure and examination of any change in the fluorescence intensity (the hydrolysis activity) by the same method as used above. The results thus obtained are plotted on FIG. 3B. It was found that the cells adapted to 30 MPa (for one hour) hydrolyzed CDCFDA at a rate approximately three times greater than that observed in the case of the cells adapted to ordinary pressure (0.1 MPa) or 60 MPa (for one hour). These results indicate that the pre-incubation of the cells at 30 MPa induced a CDCFDA-hydrolysis activity and that the activity was maintained even after releasing the applied pressure. Almost identical results were obtained when using CFDA (data not shown).

EXAMPLE 4

Dependency on Glucose Metabolism of CDCF & CDCFDA Accumulation

In this Example, there were examined the effects of D-glucose and 2-deoxyglucose on the acceleration of the hydrostatic pressure-induced accumulation of CDCF using cells of the IFO2347 strain.

The cells of the strain were cultured at 24° C. for one hour in MBA buffer containing a desired amount of D-glucose at a predetermined hydrostatic pressure (0.1 MPa (○), 30 MPa (●)) in the presence of 10 μM CDCFDA. The labeled cells were analyzed using CytoFluor 2350. The results obtained are plotted on FIG. 4A.

The cells of the IFO2347 strain were cultured at 24° C. for one hour in MBA buffer containing a desired amount of 2-deoxyglucose and 100 mM of D-glucose at a predetermined hydrostatic pressure (0.1 MPa (○), 30 MPa (●)) in the presence of 10 μM CDCFDA. The labeled cells were analyzed using CytoFluor 2350. The results obtained are plotted on FIG. 4B.

Figure 4:
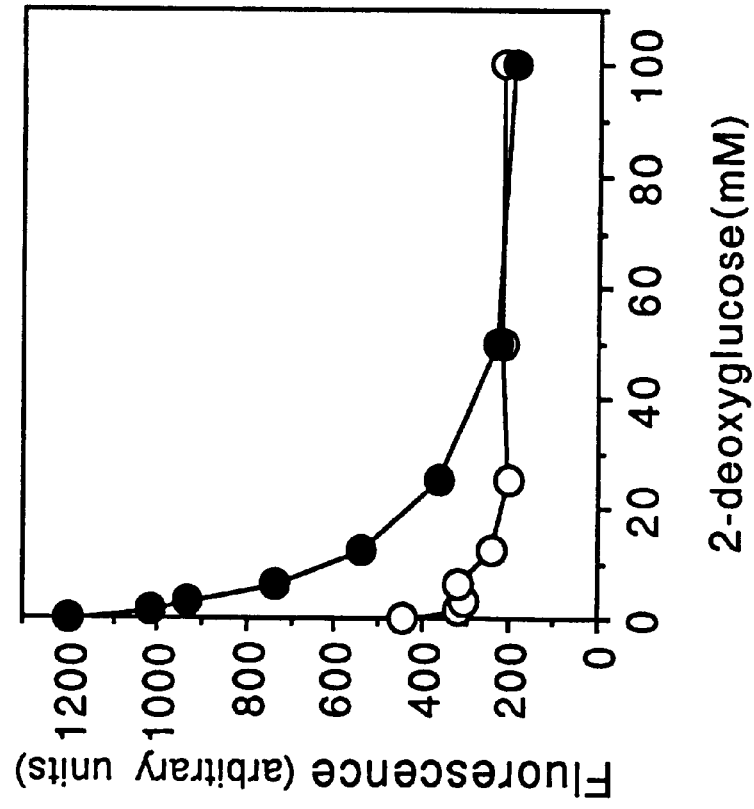
FIG. 4 is a diagram showing the influence of D-glucose and 2-deoxyglucose on the acceleration of the CDCF accumulation observed in the strain IFO2347 and induced by each hydrostatic pressure applied. (A): D-Glucose; (B) 2-Deoxyglucose+100 mM glucose.
Figure 4:
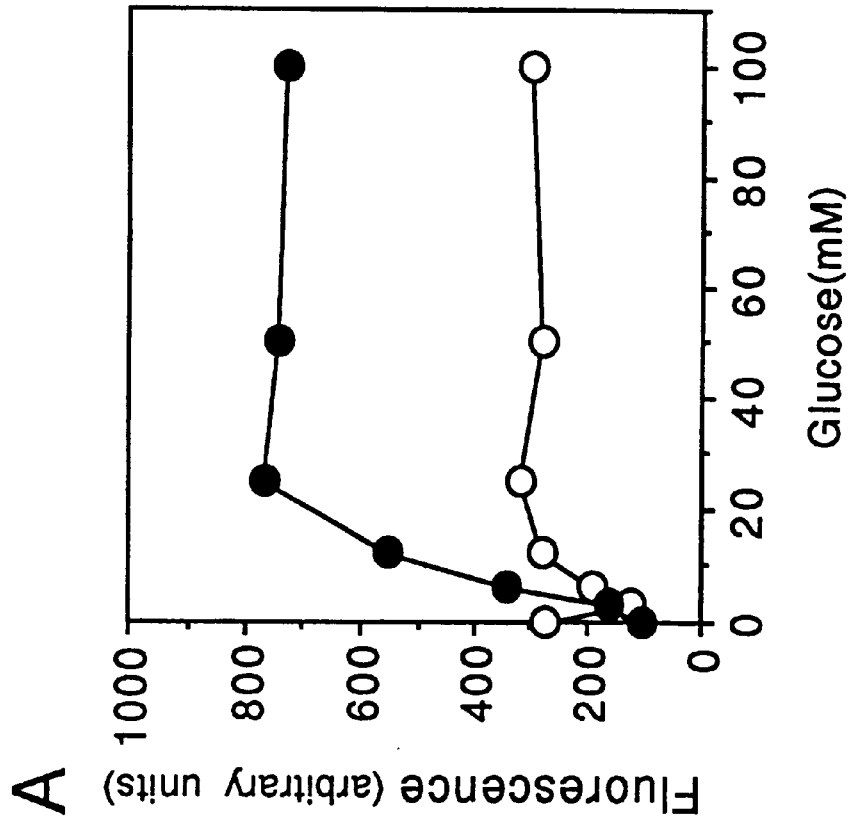

The results shown in FIG. 4A indicate that glucose is required in order to accelerate the pressure-induced accumulation of CDCF. The glucose concentration required for achieving the half-maximal CDCF accumulation was approximately 13 mM (FIG. 4A). On the other hand, it was found that 2-deoxyglucose considerably inhibited the pressure-induced accumulation of CDCF (FIG. 4B). The concentration at which half-maximal inhibition occurred was approximately 12 mM, which was very close to the glucose concentration required for achieving the half-maximal CDCF-accumulation. Both of these values were slightly lower than the Km value (20 mM) of the low affinity site of the hexose transporter (see Reference Nos. 3 and 4), but they were much greater than the Km values (<<1 mM) for sugar kinases. This suggests that the glucose metabolism or ATP production is take part in the process of CDCF accumulation.

Breeuwer et al. noted that the fluorescence intensity of labeled yeast cells depends on the following two points. That is, (i) the intracellular concentration (the amount) of the fluorescent product, which is dependent on the uptake of prefluorochrome, esterase activity, and efflux of fluorescent products, and (ii) the intracellular pH. The investigation of the dependence on pressure of the kinetics of a simple chemical reaction permits a direct measurement of the volume change associated with the formation of an activated state during the reaction. The results of preliminary experiments suggest that the hydrolysis of CFDA and CDCFDA in both MB buffer and cell extract is simply accelerated by the loading of a hydrostatic pressure. This means the chemical reaction of dye hydrolysis (the hydrolysis reaction of these fluorescent substances) accompanies negative volume changes:

$$\Delta V_+^\ddagger < 0$$

Pre-incubation of cells at a pressure of 30 MPa promoted the accumulation of CDCF, suggesting that the hydrostatic pressure may (i) induce the synthesis of esterases, (ii) promote the hydrolytic activity of esterases, (iii) promote the passive diffusion of prefluorochrome CDCFDA through the cell membrane, or (iv) stimulate a certain route of glucose metabolism, required for dye hydrolysis at 30 MPa.

As has been described above in detail, the present invention permits a significant increase in the uptake of a fluorescent substance by applying, to a sample, a non-lethal hydrostatic pressure on the order of 30 to 50 MPa (about 300 to 500atm) without causing any reduction of the survival rate of microorganisms. In this regard, when the microorganisms are detected using the existing flow cytometly system, the detection sensitivity would increase up to 5 to 10 times that conventionally attained. The application of a hydrostatic pressure of 50 MPa to a sample for about one hour shows an effect of inhibiting the proliferation of microorganisms present therein without accompanying any reduction of the survival rate thereof. Accordingly, the present invention permits the elimination of such a secondary effect that the subject microorganism undergoes proliferation during staining the same with a fluorescent dye. Thus, the present invention would contribute to the determination of the correct viable count in a wide variety of technical fields.

REFERENCES

1. Abe, F., and K. Hoiikoshi. 1995. Hydrostatic pressure promotes the acidification of vacuoles in Saccharomyces cerevisiae. FEMS Microbiology Letters 130: 307–312.
2. Balny, C., P. Masson, and F. Travers. 1989. Some recent aspects of the use of high pressure for protein investigations in solution. High Press. Res. 2: 1–28.
3. Bisson, L. F., D. G. Fraenkel. 1983. Involvement of kinases in glucose and fructose uptake by Saccharomyces cerevisiae. Proc. Natl. Acad. Sci. U. S. A. 80:1730–1734
4. Bisson, L. F., D. M. Coons, A. L. Kruckeberg, D. A. Lewis. 1993. Yeast sugar transporters. Crit. Rev. Biochem. Mol. Biol. 28: 259–308.
5. Breeuwer, P., J.-L. Drocourt, F. M. Rombouts, and T. Abee. 1994. Energydependent, carrier-mediated extrusion of carboxyfluorescein from Saccharomyces cerevisiae allows rapid assessment of cell viability by flow cytometry. Appl. Environ. Microbiol. 60: 1467–1472.
6. Breeuwer, P., J.-L. Drocourt, N. Bunschoten, M. H. Zwietering, F. M. Rombouts, and T. Abee. 1995. Characterization of uptake and hydrolysis of fluorescein diacetate and carboxyfluorescein diacetate by intracellular esterases in Saccharomyces cerevisiae, which result in accumulation of fluorescent product. Appl. Environ. Microbiol. 61: 1614–1619.
7. Davey, H., and D. B. Kell. 1996. Flow cytometry and cell sorting of heterogeneous microbial populations: the importance of single-cell analyses. Microbiol. Rev. 60: 641–696.
8. Heremans, K. 1982. High pressure effects on proteins and other biomolecules. Annu Rev. Biophys. Bioeng. 11:1–21.
9. Preston, R. A, R. F. Murphy, and E. W. Jones. 1989. Assay of vacuolar pH in yeast and identification of acidification-defective mutants. Proc. Natl. Acad. Sci. U.S.A. 86: 7027–7031.
10. Pringle, J. R., R. A. Preston, A. E. M. Adams, T. Stearns, D. G. Drubin, B. K. Haarer, and E. W. Jones. 1989. Fluorescence microscopy methods for yeast. in Methods in Cell Biol. 31: 357–436.
11. Troussellier, M., C. Courties, and A. Vaquer. 1993. Recent applications of flow cytometry in aquatic mnicrobial ecology. Biol. Cell 78: 111–121.

What is claimed is:

1. A method for detecting microorganisms present in a sample comprising the steps of:
    staining the microorganisms with a fluorescent dye which is selected from the group consisting of carboxyfluorescein diacetate (CFDA) and carboxydichlorofluorescein diacetate (CDCFDA), wherein staining is effected concurrent with the application of a non-lethal hydrostatic pressure, which treatment comprises applying a pressure for a time sufficient to enhance the accumulation of said fluorescent dye by said microorganisms five to ten fold greater than the amount of said dye which would otherwise be accumulated by said microorganisms at atmospheric pressure, and wherein said microorganisms are yeast.

2. The method for detecting microorganisms of claim 1 wherein the hydrostatic pressure which is applied ranges from 30 to 50 MPa.

3. A method for increasing the uptake of fluorescent dye molecules by microorganisms present in a sample, comprising the steps of:
  (i) adding to said sample a fluorescent dye which is selected from the group consisting of carboxyfluorescein diacetate (CFDA) and carboxydichlorofluorescein diacetate (CDCFDA), and
  (ii) applying a non-lethal hydrostatic pressure to said sample comprising microorganisms, wherein said hydrostatic pressure is applied at a pressure and for a time sufficient to enhance the accumulation of said fluorescent dye by said detected microorganisms five to ten fold greater than the accumulation by said detected microorganisms which would result at ambient pressure, and
wherein said microorganisms are yeast.

4. The method for increasing the uptake of fluorescent dye molecules according to claim 3 wherein the hydrostatic pressure which is applied ranges from 30 to 50 MPa.

5. A method for detecting microorganisms present in a sample comprising the steps of:
  staining the microorganisms with a fluorescent dye which is selected from the group consisting of carboxyfluorescein diacetate (CFDA) and carboxydichlorofluorescein diacetate (CDCFDA), wherein staining is effected after the application of a non-lethal hydrostatic pressure and wherein said microorganism is yeast.

* * * * *

UNITED STATES PATENT AND TRADEMARK OFFICE
CERTIFICATE OF CORRECTION

PATENT NO.   : 6,358,700 B2  
DATED        : March 19, 2002  
INVENTOR(S)  : Fumiyoshi Abe et al.

It is certified that error appears in the above-identified patent and that said Letters Patent is hereby corrected as shown below:

<u>Title page,</u>  
Item [75], name of first Inventor is corrected to read -- Fumiyoshi ABE --.

Signed and Sealed this

Twenty-seventh Day of August, 2002

Attest:

Attesting Officer

JAMES E. ROGAN  
*Director of the United States Patent and Trademark Office*